United States Patent [19]

Harnisch

[11] 4,278,795
[45] Jul. 14, 1981

[54] PROCESS FOR THE PREPARATION OF PYRENE COMPOUNDS

[75] Inventor: Horst Harnisch, Much, Fed. Rep. of Germany

[73] Assignee: Bayer Aktiengesellschaft, Leverkusen, Fed. Rep. of Germany

[21] Appl. No.: 141,833

[22] Filed: Apr. 21, 1980

[30] Foreign Application Priority Data

Jun. 8, 1979 [DE] Fed. Rep. of Germany ....... 2923337

[51] Int. Cl.³ .......................................... C07D 251/16
[52] U.S. Cl. ......................................... 544/219; 544/4
[58] Field of Search ................................... 544/4, 219

[56] References Cited

U.S. PATENT DOCUMENTS 3,157,651  11/1964  Atkinson et al. .................... 544/219
3,975,291  8/1976  Claussen et al. .................... 544/219

Primary Examiner—John M. Ford
Attorney, Agent, or Firm—Sprung, Felfe, Horn, Lynch & Kramer

[57] ABSTRACT

The preparation of pyrene compounds of the formula

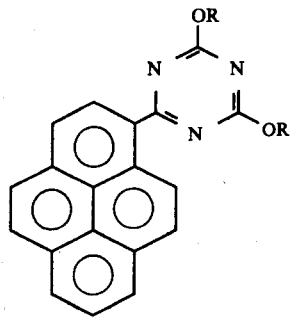

wherein
R represents an optionally substituted alkyl, alkenyl, cycloalkyl, aralkyl or aryl radical, by reaction of cyanuric chloride with pyrene in the presence of an aluminium halide and then reaction of the product with a compound M—OR (M = an alkali metal) can be improved by allowing a complex of an aluminium halide and cyanuric chloride to act on pyrene and reacting the product with a compound

RO—M

The compounds of the formula I are known optical brighteners.

9 Claims, No Drawings

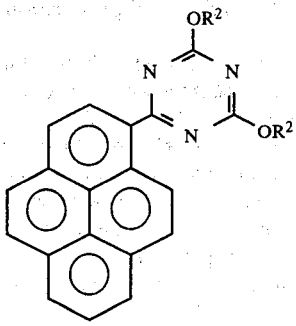

which likewise have valuable whitener properties, for example for the optical brightening of polyester materials.

These compounds are obtained by a procedure in which, instead of a single compound of the formula RO—M, wherein R has the abovementioned meaning, an equivalent mixture of components of the formulae R¹OM and R²OM, wherein R¹ and R² are different and each have one of the meanings given for R, is employed in the process according to the invention.

In practice, the process is appropriately carried out by a procedure in which an aluminium halide is stirred with at least an equivalent amount of cyanuric chloride in an inert solvent at 0°–25° C., preferably 10°–20° C., for several hours, pyrene is allowed to act on the resulting colourless cyanuric chloride-aluminium halide complex at 0°–25° C., preferably 10°–20° C., whilst cooling, whereupon the deep blue aluminium halide complex forms, this complex is mixed, advantageously without intermediate isolation, at 0°–40° C., preferably 0°–25° C., with intense cooling, with the compound of the formula RO—M, wherein R has the abovementioned meaning, in an amount which is at least equivalent for the total number of replaceable halogen atoms present, the reaction mixture is then heated briefly to 50°–80° C., preferably 60°–75° C., advantageously in an inert gas atmosphere, heating to 60° C. and above extending over 5 hours appropriately being avoided, the reaction mixture is allowed to cool and the process product is isolated and washed first with a polar, water-miscible organic solvent, such as methanol or ethanol, and finally with water.

As mentioned above, the end product is as a rule obtained in such a high purity that no additional purification operations are necessary.

Examples of suitable inert solvents are halogenated hydrocarbons or nitro-hydrocarbons, such as methylene chloride, chloroform, carbon tetrachloride, 1,2-dichloroethane, hexachloroethane, chlorobenzene, o-dichlorobenzene, chlorotoluene, dichlorotoluene, trichlorobenzene, nitromethane, nitropropane and nitrobenzene. The aromatic chlorinated hydrocarbons and nitro-hydrocarbons, in particular o-dichlorobenzene, trichlorobenzene and nitrobenzene, are preferred.

Possible aluminium halides are aluminium bromide and, in particular, aluminium chloride.

The compounds of the formula RO—M can advantageously be employed as a solution in the ROH compound concerned, if this is liquid, for example as a 30% strength methanolic sodium methylate solution, or they can be employed with equal success as a mixture of compounds of the formula ROH and alkali metal hydroxides of the formula MOH.

Only 1–1.1 mols of aluminium halide and 1–1.2 mols of cyanuric chloride are appropriately employed per mol of pyrene. It is important that as far as possible free aluminium halide is no longer present during the addition of pyrene.

For the total number of replaceable halogen atoms present in the reaction mixture, at least 6 equivalents of the compound of the formula RO—M are required per mol of pyrene, that is to say 3 equivalents for the cyanuric chloride and 3 equivalents for the aluminium halide. 6.5–9.5 equivalents are appropriately used.

EXAMPLE 1

243.6 g (1.32 mols) of cyanuric chloride and 168 g (1.26 mols) of anhydrous aluminium chloride powder are added successively to 2,000 ml of anhydrous o-dichlorobenzene at 15°–18° C. and the mixture is stirred in this temperature range for 8 hours. 242.4 g (1.2 mols) of powdered pyrene are then added at the above temperature, whilst cooling (30–60 minutes). During this addition, care should be taken that the components are mixed thoroughly and local overheating should be avoided. The deep blue-violet suspension is subsequently stirred at 15°–18° C. for 2 hours. 1,800 g of 30% strength methanolic sodium methylate solution (10 mols) are now added at 10°–18° C., with intense cooling (1.5 hours), the mixture is stirred for a further 6 hours at <20° and then at 70° C. (reflux) for 30 minutes and is left to cool. The crystalline precipitate is filtered off at room temperature and washed twice with a total of 1 l of methanol and the material on the filter is pressed off well, washed in several portions with a total of 16 l of water and dried at 90° C. in vacuo.

Yield: 344 g (84.5% of theory) of 1-(2,4-dimethoxy-1,3,5-triazin-6-yl)-pyrene of melting point 199° C. Additional purification is not necessary.

If, instead of o-dichlorobenzene, an equal volume of anhydrous nitrobenzene is used, 352 g (86% of theory) of an equally pure 1-(2,4-dimethoxy-1,3,5-triazin-6-yl)-pyrene are obtained.

EXAMPLE 2

250 g (1.36 mols) of cyanuric chloride and 168 g (1.26 mols) of anhydrous aluminium chloride powder are successively added to 800 ml of anhydrous o-dichlorobenzene at 15°–18° C. and the mixture is stirred in the given temperature range for 12 hours. A solution of 242.4 g (1.2 mols) of pyrene in 1 l of anhydrous o-dichlorobenzene is then added, initially drop by drop, also at 15°–18° C., whilst cooling, and the deep blue-violet suspension is subsequently stirred at 15°–18° C. for 2 hours.

1,760 g of 30% strength sodium methylate solution are initially introduced into a 2nd reaction vessel. With the aid of a glass tube immersed as deeply as possible in the stirred suspension of the AlCl₃ complex, this suspension is drawn dropwise, with a slightly reduced pressure, into the intensely cooled sodium methylate solution at 10°–15° C., whilst stirring (3 hours). The 1st reaction vessel is then rinsed out with 200 ml of anhydrous o-dichlorobenzene and the suspension thus obtained is drawn into the methylate solution at 10°–15° C. in the same way. The mixture is subsequently stirred for a further 6 hours at below 20° C. and is then heated to the boiling point under N₂ for 1 hour. After cooling to

PROCESS FOR THE PREPARATION OF PYRENE COMPOUNDS

The present invention relates to a process for the preparation of compounds of the formula

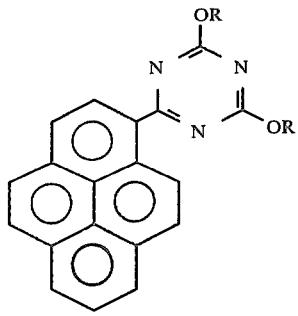

wherein
R represents an optionally substituted alkyl, alkenyl, cycloalkyl, aralkyl or aryl radical.

Such compounds have achieved industrial importance as optical brighteners for textile materials such as polyesters and plastics. They have hitherto been prepared by a procedure in which aluminum chloride is introduced into a mixture of pyrene and cyanuric chloride in a suitable solvent and, after methanolysis or hydrolysis, the reaction product is isolated, freed from aluminium salts by stirring with ice-cold hydrochloric acid, isolated again, washed with methanol and dried and the chlorine atoms are replaced by RO radicals in a further reaction step (U.S. Pat. No. 2,232,871, British Pat. No. 985,484 and British Pat. No. 1,221,930).

However, this method of preparation has a number of disadvantages. In particular, the yields and purity of the process products leave something to be desired. There has thus been no lack of attempts to improve the preparation. Thus, for the specific case where R is methyl, the reaction of 2-chloro-4,6-dimethoxy-triazine, which is to be prepared from cyanuric chloride in a separate reaction step, with pyrene in the presence of aluminium chloride is recommended in British Pat. No. 1,144,002. However, according to the statements of the Patent Specification, even this process gives a yield of only 55%.

The object of the present invention was thus to develop a rational process which leads to purer products.

This object is now achieved, according to the invention, by a procedure in which a complex is prepared by reacting an aluminium halide with at least an equivalent amount of cyanuric chloride in an inert solvent, this complex is allowed to act on pyrene and the product is reacted, advantageously without intermediate isolation, with a compound of the formula

RO—M    (II)

wherein
R has the abovementioned meaning and
M represents an alkali metal, preferably sodium or potassium, in an amount which is at least equivalent for the replaceable halogen atoms.

This process gives high yield of, as a rule, 80–90% of theory, relative to the pyrene.

The process products are obtained in such a high purity that additional purification is in general unnecessary.

The reaction product formed in the action of pyrene on the colourless cyanuric chloride-aluminium halide complex is a blue 1-(2,4-dichloro-1,3,5-triazin-6-yl)-pyrene hydrochloride-aluminium halide complex which, surprisingly, reacts with compounds of the formula II more readily and more completely than 1-(2,4-dichloro-1,3,5-triazin-6-yl)-pyrene itself, which was hitherto prepared from the complex by subsequent methanolysis or hydrolysis and then removal of the aluminium salts.

It is also surprising that the process according to the invention proceeds so smoothly and gives the process products in such excellent yields and purity since the acylation of hydrocarbons in the presence of Friedel-Crafts catalysts in most cases does not proceed quantitatively and the aluminium salts in general interfere in subsequent reactions, so that the acylation products must as a rule be hydrolysed, isolated and purified before they can be used in further reactions.

It is also surprising that the relatively large excess of catalyst (as a rule 50 mol%), and thus in the present case also cyanuric chloride, otherwise required for Friedel-Crafts acylations of hydrocarbons can largely be dispensed with. This has the decisive advantage that, in the subsequent reaction with alcoholate or phenolate, a much too high a salt load and the necessary increase in reaction volume associated therewith can be avoided.

The new process is particularly suitable for the preparation of those compounds of the formula I
wherein
R represents $C_1$–$C_5$-alkyl which is optionally substituted by hydroxyl, $C_1$–$C_4$-alkoxy or phenoxy,
$C_2$–$C_5$-alkenyl, cyclohexyl or a phenyl-$C_1$–$C_3$-alkyl or phenyl radical which is optionally substituted by methyl or chlorine.

$C_1$–$C_4$-Alkyl radicals, and in particular methyl, are particularly preferred for R.

The new process is also particularly suitable for the preparation of mixtures of compounds of the formulae

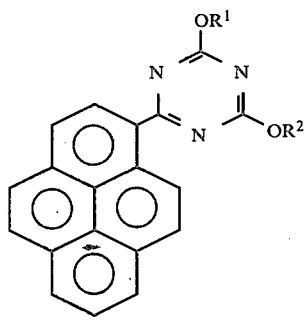

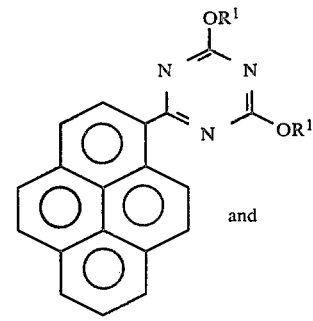

and

20° C. and stirring at this temperature for 3 hours, the crystalline precipitate is filtered off and washed with 1 l of methanol and the material on the filter is pressed off well and washed with a large amount of water.

Yield (moist): 630 g ≙ 348 g of dry weight ≙ 85% of theory.

Melting point: 199.5°–200° C.

EXAMPLE 3

121.8 g (0.66 mol) of cyanuric chloride and 84 g (0.63 mol) of anhydrous aluminium chloride powder are stirred in 1 l of anhydrous o-dichlorobenzene at below 20° C. After 4 hours, a suspension of 121.2 g (0.6 mol) of pyrene in 350 ml of o-dichlorobenzene is added at below 20° C., whilst cooling.

The mixture is subsequently stirred for a further 2 hours at below 20°. 331 g of 2-phenoxyethanol are now added at 20°–25° C., 307.4 g of potassium hydroxide powder (technical grade, 88% pure, 4.83 mols) are gradually added at 10°–20° C., with intense cooling, and the mixture is subsequently allowed to react at below 20° for 5 hours. The crystalline precipitate is filtered off, washed with 500 ml of methanol and with 4 l of water and dried at 80° C. in vacuo. Yield: 269 g (81% of theory) of 1-(2,4-di-β-phenoxyethoxy-1,3,5-triazin-6-yl)-pyrene of melting point 185°–186° C. Additional purification is not necessary.

EXAMPLE 4

The procedure followed is as according to the statements of Example 1, but a mixture of 870 g of 30% strength methanolic sodium methylate solution and 1,636 g of 20% strength ethanolic sodium ethylate solution is employed instead of the sodium methylate solution. Yield: 360 g of a mixture of 1-(2,4-dimethoxy-1,3,5-triazin-6-yl)-pyrene, 1-(2,4-diethoxy-1,3,5-triazin-6-yl)-pyrene and 1-(2-methoxy-4-ethoxy-1,3,5-triazin-6-yl)-pyrene of melting point 151°–157° C.

EXAMPLE 5

If the procedure followed is as according to the statements of Example 3, but instead of 2-phenoxyethanol, equivalent amounts of the alcohols listed below are used, the corresponding oxytriazinylpyrenes are obtained, in the yields shown in brackets: allyl alcohol (81%), benzyl alcohol (87%), n-butanol (88%), methoxyethanol (86%), hydroxyethanol (83%), cyclohexanol (78%) and γ-phenyl-n-propanol (82%).

I claim:

1. Process for the preparation of pyrene compounds of the formula

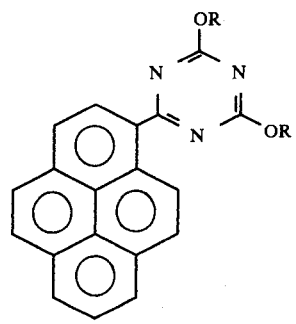

wherein
R represents an optionally substituted alkyl, alkenyl, cycloalkyl, aralkyl or aryl radical, by reaction of cyanuric chloride with pyrene in the presence of an aluminium halide and by further reaction of the intermediate product with an alkali metal alcoholate or phenolate, characterised in that a complex is prepared by reacting an aluminium halide with at least an equivalent amount of cyanuric chloride in an inert solvent, this complex is allowed to act on pyrene and the product is reacted with a compound of the formula

RO—M wherein
R has the abovementioned meaning and
M represents an alkali metal, in an amount which is at least equivalent for the replaceable halogen atoms.

2. Process according to claim 1, characterised in that neither the complex of cyanuric chloride and the aluminium halide nor the reaction product obtained therefrom by the action of pyrene is intermediately isolated.

3. Process according to claim 1, characterised in that $AlCl_3$ is used as the aluminium halide.

4. Process according to claim 1, characterised in that, per mol of pyrene, 1–1.1 mols of aluminium halide and 1–1.2 mols of cyanuric chloride are used for the preparation of the cyanuric chloride-aluminium halide complex.

5. Process according to claim 1, characterised in that the reaction of the aluminium halide with cyanuric chloride and the subsequent reaction with pyrene are carried out at 0°–25° C., the compound RO—M is mixed with the reaction product of the cyanuric chloride-aluminium halide complex and pyrene at 0°–40° C. and the replacement reaction is brought to completion by warming the mixture to 50°–80° C.

6. Process according to claim 1, characterised in that, per mol of pyrene, 6.5–9.5 mols of compound of the formula RO—M are used for replacing halogen by the radicals of the formula RO—.

7. Process according to claim 1, characterised in that the suspension of the reaction product of the cyanuric chloride-aluminium halide complex and pyrene in the inert organic solvent is introduced into a cooled solution of RO—M in RO—H.

8. Process according to claim 1, characterised in that compounds of the formula RO—M are used in the form of mixtures of ROH and MOH.

9. Process according to claim 1, characterised in that, instead of a single compound of the formula RO—M, an equivalent mixture of components of the formulae $R^1O—M$ and $R^2O—M$ wherein
$R^1$ and $R^2$ are different and each have one of the meanings given for R, is used.

* * * * *